US 9,700,396 B2

(12) United States Patent
Taylor

(10) Patent No.: US 9,700,396 B2
(45) Date of Patent: Jul. 11, 2017

(54) URETHRA CLAMP

(71) Applicant: Coloplast A/S, Humlebaek (DK)

(72) Inventor: Jeffrey Brian Taylor, Forest Lake, MN (US)

(73) Assignee: Coloplast A/S, Humlebaek (DK)

( * ) Notice: Subject to any disclaimer, the term of this patent is extended or adjusted under 35 U.S.C. 154(b) by 98 days.

(21) Appl. No.: 14/516,587

(22) Filed: Oct. 17, 2014

(65) Prior Publication Data

US 2016/0089224 A1   Mar. 31, 2016

Related U.S. Application Data

(60) Provisional application No. 62/057,555, filed on Sep. 30, 2014.

(51) Int. Cl.
| | | |
|---|---|---|
| *A61F 2/02* | (2006.01) | |
| *A61F 2/00* | (2006.01) | |
| *A61B 17/122* | (2006.01) | |
| *A61B 17/00* | (2006.01) | |

(52) U.S. Cl.
CPC .......... *A61F 2/004* (2013.01); *A61B 17/1227* (2013.01); *A61B 2017/00557* (2013.01); *A61B 2017/00805* (2013.01); *A61F 2230/0013* (2013.01); *A61F 2250/001* (2013.01); *A61F 2250/0003* (2013.01); *A61F 2250/0013* (2013.01)

(58) Field of Classification Search
CPC .............. A61F 2/004; A61F 2230/0013; A61F 2250/001; A61F 2250/0013; A61F 2250/0003; A61B 2017/00805; A61B 17/1227; A61B 2017/00557

USPC ................................ 600/29–31; 128/897–899
See application file for complete search history.

(56) References Cited

U.S. PATENT DOCUMENTS

| | | | | |
|---|---|---|---|---|
| 3,744,063 A | * | 7/1973 | McWhorter | ............ A61F 2/004 |
| | | | | 128/DIG. 25 |
| 3,815,576 A | * | 6/1974 | Balaban | ................. A61F 2/004 |
| | | | | 128/DIG. 25 |
| 4,063,548 A | | 12/1977 | Klatt et al. | |
| 4,191,196 A | | 3/1980 | Bradley et al. | |
| 4,222,377 A | * | 9/1980 | Burton | .................... A61F 2/004 |
| | | | | 128/DIG. 25 |

(Continued)

FOREIGN PATENT DOCUMENTS

| | | |
|---|---|---|
| DE | 2438691 A1 | 2/1976 |
| EP | 1238638 A1 | 9/2002 |
| FR | 2688693 A1 | 9/1993 |

OTHER PUBLICATIONS

AMS 800 Urinary Control System, Operating Room Manual, Mar. 2004.

*Primary Examiner* — Navin Natnithithadha
*Assistant Examiner* — Sunita Reddy
(74) *Attorney, Agent, or Firm* — Coloplast Corp., Coloplast A/S; Nick Baumann

(57) ABSTRACT

An artificial urinary sphincter (AUS) system that includes a clamp and an inflatable device. The clamp is configured to be disposed on a urethra and includes a first portion and a second portion biased together to compress the urethra. The inflatable device is coupled between the first portion and the second portion of the clamp and configured to be inflated to separate the first portion from the second portion and unclamp or open the urethra.

8 Claims, 6 Drawing Sheets

(56) References Cited

U.S. PATENT DOCUMENTS

| | | | | |
|---|---|---|---|---|
| 4,412,530 | A * | 11/1983 | Burton | A61F 2/004 128/DIG. 25 |
| 4,556,050 | A * | 12/1985 | Hodgson | A61F 2/004 128/DIG. 25 |
| 4,878,889 | A * | 11/1989 | Polyak | A61F 2/004 128/DIG. 25 |
| 4,909,785 | A * | 3/1990 | Burton | A61F 2/0027 604/544 |
| 4,932,956 | A | 6/1990 | Reddy et al. | |
| 4,932,958 | A | 6/1990 | Reddy et al. | |
| 4,994,020 | A | 2/1991 | Polyak | |
| 5,078,720 | A | 1/1992 | Burton et al. | |
| 5,335,669 | A | 8/1994 | Tihon et al. | |
| 5,356,423 | A | 10/1994 | Tihon et al. | |
| 5,496,271 | A | 3/1996 | Burton et al. | |
| 5,499,994 | A | 3/1996 | Tihon et al. | |
| 5,518,504 | A * | 5/1996 | Polyak | A61F 2/0036 128/DIG. 25 |
| 5,720,415 | A | 2/1998 | Morningstar | |
| 5,895,356 | A | 4/1999 | Andrus et al. | |
| 6,382,214 | B1 | 5/2002 | Raz et al. | |
| 6,460,262 | B1 | 10/2002 | Cabak et al. | |
| 6,558,315 | B1 | 5/2003 | Kuyava | |
| 6,612,977 | B2 | 9/2003 | Staskin et al. | |
| 6,616,653 | B2 | 9/2003 | Beyar et al. | |
| 6,652,450 | B2 | 11/2003 | Neisz et al. | |
| 6,802,807 | B2 | 10/2004 | Anderson et al. | |
| 6,971,986 | B2 | 12/2005 | Staskin et al. | |
| 7,015,253 | B2 | 3/2006 | Escandon et al. | |
| 7,048,682 | B2 | 5/2006 | Neisz et al. | |
| 7,083,568 | B2 | 8/2006 | Neisz et al. | |
| 7,267,645 | B2 | 9/2007 | Anderson et al. | |
| 7,291,104 | B2 | 11/2007 | Neisz et al. | |
| 7,315,762 | B2 | 1/2008 | Mosher et al. | |
| 2007/0167962 | A1 * | 7/2007 | Gannoe | A61B 17/00234 606/153 |
| 2009/0012350 | A1 * | 1/2009 | Tihon | A61B 17/282 600/30 |
| 2009/0018385 | A1 * | 1/2009 | Trubiano | A61F 2/0036 600/30 |
| 2009/0306460 | A1 * | 12/2009 | Stephens | A61N 1/36007 600/30 |
| 2010/0160716 | A1 * | 6/2010 | Snow | A61F 2/004 600/31 |
| 2012/0157759 | A1 * | 6/2012 | Wirbisky | A61F 2/004 600/31 |

* cited by examiner

URETHRA CLAMP

BACKGROUND

Urinary incontinence affects many people and is a worldwide health issue. Published research indicates that urinary incontinence presents a substantial social and economic burden worldwide, affecting up to a mean of about 16% of the global population.

Urinary incontinence in women can be associated with a prolapse of one or more pelvic organs, which can arise from child birth or a weakness in the tissues/muscle of the pelvic floor. Urinary incontinence in men can arise after surgical treatment of the prostate gland, which treatment can include removal or weakening of the prostatic sphincter of the urinary urethra.

One treatment for urinary incontinence includes placing an artificial sphincter around a circumference of a portion of the urethra. The artificial sphincter operates to compress the urethra to selectively coapt or stop the flow of urine through the urethra, thus providing the user with a continent state. The artificial sphincter can be activated to an open position by the user, which opens the urethra and allows the user to selectively pass urine.

Surgeons and patients would welcome advances in the treatment of urinary incontinence.

SUMMARY

Some embodiments of the disclosure provide an artificial urinary sphincter (AUS) system, including a clamp and an inflatable device. The clamp is configured to be disposed on a urethra and includes a first portion and a second portion biased together to compress the urethra. The inflatable device is coupled between the first portion and the second portion of the clamp and configured to be inflated to separate the first portion from the second portion and unclamp or open the urethra.

Some embodiments of the disclosure provide a method including the steps of biasing a first portion and a second portion of a clamp toward each other to compress a urethra, and inflating a device, coupled to the first portion and the second portion, to push the first portion away from the second portion and unclamp or open the urethra.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
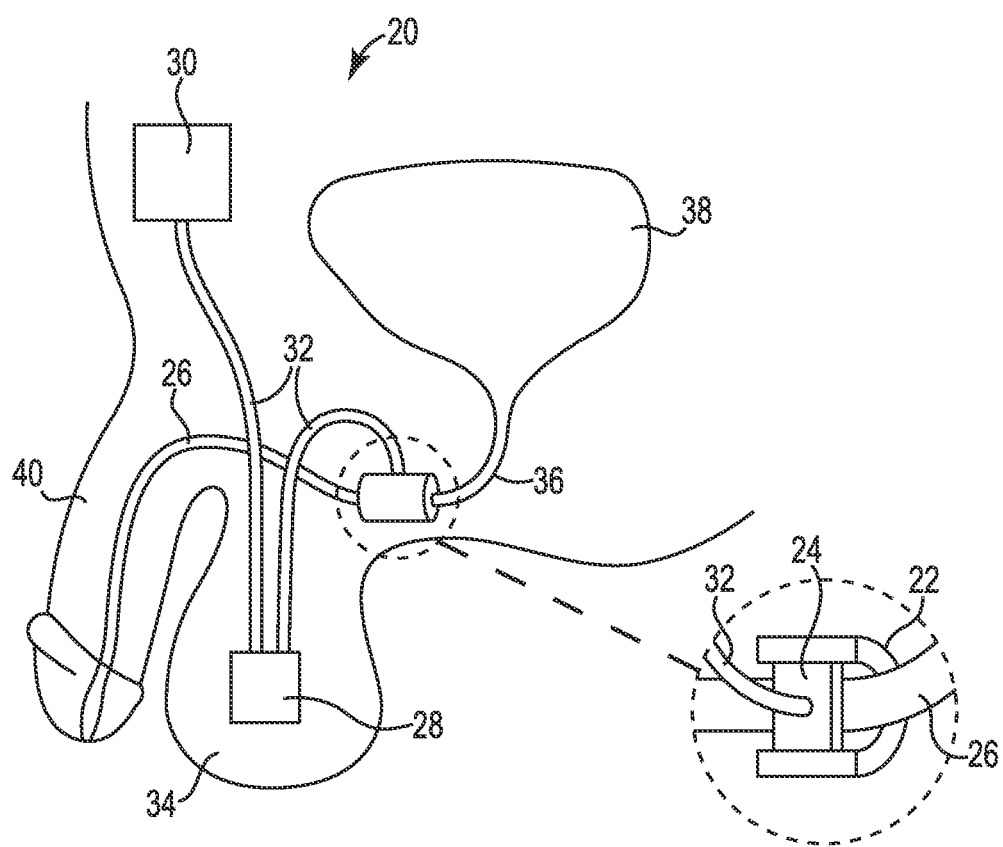
FIG. 1 is a perspective view of one embodiment of an AUS system illustrated as implanted in the environment of the male urogenital region.

In the following Detailed Description, reference is made to the accompanying drawings, which form a part hereof, and in which is shown by way of illustration embodiments. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the disclosure. The following detailed description, therefore, is not to be taken in a limiting sense.

The features of the various exemplary embodiments described in this disclosure may be combined with each other ("mixed and matched"), unless specifically noted otherwise.

Soft tissue includes dermal tissue, sub-dermal tissue, ligaments, tendons, or membranes but does not include bone.

End means endmost. A distal end is the furthest endmost location of a distal portion of a thing being described, whereas a proximal end is the nearest endmost location of a proximal portion of the thing being described. The portion next to or adjacent to an end is an end portion.

Artificial urinary sphincters have proved useful in the treatment of urinary incontinence. An AUS is implanted around the urethra and is operable to selectively coapt the lumen of the urethra to allow the user to shift the artificial sphincter from an open state that allows urine to pass to a closed state that provides the user with continence.

One urinary control system that has found favor with the medical community includes three components cooperatively attached with tubing. The three components include an occlusive cuff, a control pump, and a pressure-regulating balloon reservoir. The cuff is implanted around the urethra, the control pump is implanted in the scrotum of a male user, and the pressure-regulating balloon reservoir is implanted in the prevesical space. The three components are filled with a liquid to provide a liquid-filled closed system that is maintained at an equilibrium pressure that closes the cuff around the urethra. When the user wishes to void, he squeezes and releases the pump several times to move fluid from the cuff into the pressure-regulating balloon reservoir. The cuff "deflates" and opens, which allows the urethra to open and pass urine. The pressure-regulating balloon reservoir, having been pressurized to a pressure above the equilibrium pressure by action of the pump, eventually automatically re-pressurizes the cuff to the equilibrium pressure over the course of several minutes to again inflate the cuff and coapt the urethra. The cuff is fabricated from sheets of film that are sealed to provide one or more inflatable cushions. The cuff is provided in a rectangular shape and intended to be placed around the urethra, with the ends of the rectangular cuff secured together. However, observers have noticed that the cuff of this system has a tendency to kink when it inflates, particularly at the junction of where the rectangular balloon cushions are formed into a circular cuff. The location of this kink can wear over time and create a leak in the cuff.

Embodiments described in this disclosure provide an AUS system that includes a clamp configured for placement around the urethra. The clamp includes first and second portions that are biased together to compress the urethra. The AUS system further includes at least one device that is coupled to the first and second portions and configured to be inflated to separate the first portion from the second portion and open the urethra. Embodiments described in this disclosure also provide an AUS system that includes a clamp that includes first and second rigid members elastically biased together to compress the urethra and at least one device that is coupled to the first and second rigid members and configured to be inflated to push the first rigid member away from the second rigid member and open the urethra.

In some embodiments, the clamp is a single C-shaped piece of material having a first portion, a second portion, and a deformable end situated between the first portion and the second portion, where the deformable end biases the first portion and the second portion together to compress the urethra. In some embodiments, the clamp includes separate first and second portions, which are biased together to compress the urethra.

Embodiments of the AUS system described in this disclosure further include a fluid reservoir that holds a fluid, such as a saline solution, and a pump that moves the fluid from the reservoir to the inflatable device to separate the first and second portions or the first and second rigid members and open the urethra.

The AUS systems described in this disclosure are suited for use in both female patients and male patients, where the clamp is placed around a portion of the urethra. Female patients can have the pump component implanted in one of the labia or an abdominal area. Male patients can have the pump component implanted in the scrotum.

FIG. 1 is a perspective view of one embodiment of an AUS system 20 illustrated as implanted in the environment of the male urogenital region. The AUS system 20 includes a clamp 22 and at least one inflatable device 24, which are situated around the urethra 26. The AUS system 20 also includes a pump 28 that is fluidically coupled to the inflatable device 24 and to a fluid reservoir 30 via tubing 32, such as kink-resistant tubing.

The clamp 22 includes multiple portions or members that are situated on opposing sides of the urethra 26 and biased together to compress the urethra 26 and prevent incontinence. The inflatable device 24 is coupled to the clamp 22 and configured to be inflated to separate the portions or members of the clamp 22 and open the urethra 26 for voiding. In some embodiments, the inflatable device 24 includes at least one balloon that is inflated to expand the inflatable device 24 and separate the portions or members of the clamp 22.

The pump 28 and the fluid reservoir 30 are operable to inflate the inflatable device 24. The fluid reservoir 30 is sized to retain a volume of liquid that can be moved into the inflatable device 24 to expand the inflatable device 24 and open the urethra 26.

In some embodiments, the pump 28 is a pump bulb that, upon squeezing, moves the fluid from the fluid reservoir 30 to the inflatable device 24. This expands the inflatable device 24 and separates the portions or members of the clamp 22 to open the urethra 26 for voiding. In some of these embodiments, the inflatable device 24 automatically deflates over time, such as 2 or 3 minutes or less, through a leaky valve arrangement in the pump 28 and the inflatable device 24, where the bias of the clamp 22 assists in deflating the inflatable device 24. After deflating the inflatable device 24, the portions or members of the clamp 22 compress the urethra 26 to prevent incontinence. In some embodiments, other suitable pumps are used, such as electromechanical pumps, electronic pumps, and button-style cavity pumps.

In some embodiments, the fluid reservoir 30 provides a regulated fluid pressure and the pump 28 includes a control valve that, upon activation, allows the fluid to move from the fluid reservoir 30 to the inflatable device 24. This expands the inflatable device 24 and separates the portions or members of the clamp 22 to open the urethra 26 for voiding. In some of these embodiments, the pump 28 includes a pump bulb that, upon squeezing, moves the fluid from the inflatable device 24 to the fluid reservoir 30 to deflate the inflatable device 24, where the bias of the clamp 22 assists in deflating the inflatable device 24. After deflating the inflatable device 24, the portions or members of the clamp 22 compress the urethra 26 to prevent incontinence. In some embodiments, other suitable pumps are used, such as electromechanical pumps, electronic pumps, and button-style cavity pumps.

The pump 28 can be implanted within the scrotum 34, which provides access to the pump 28 by the user. Also, other locations for placement of the pump 28 are acceptable, for example as determined by the gender of the user.

The tubing 32 is provided in a kink resistant form and includes some style of connector that allows segments of the tubing 32 to be attached together after the various components, such as the pump 28 and the fluid reservoir 30, are primed with liquid. The tubing 32 is a thin-walled tube that is attachable between the pump 28 and the fluid reservoir 30, and between the pump 28 and the inflatable device 24. In one embodiment, the tubing 32 is separate from the pump 28 and separate from the fluid reservoir 30 and connects to these components through a locking mechanism, such as a quick connector or other suitable snap-fit connector.

The clamp 22 is implanted around the bulbous urethra or around the portion of the urethra 26 descending from the bladder neck 36. The clamp 22 is sized to allow placement as close to the bladder 38 as possible (desired by some surgeons), or positioned distal the bladder neck 36 as suitably determined by the attending surgeon. As illustrated in FIG. 1, the clamp 22 is implanted around the urethra 26 at a location where the urethra 26 transitions from a vertical orientation communicating with the bladder 38 to a horizontal orientation extending to the penis 40, which desirably corresponds to the area of the urogenital region associated with an increased level of muscle mass.

Figure 2A:
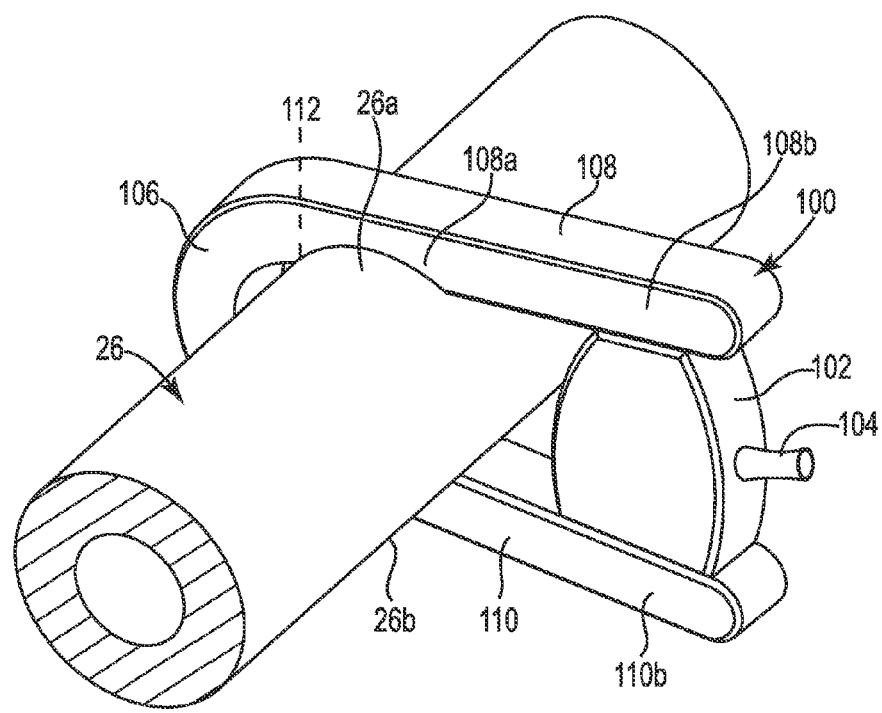
FIG. 2A is a perspective view of one embodiment of a clamp and an inflatable device situated on the urethra, where the inflatable device is expanded to open the urethra for voiding.
Figure 2B:
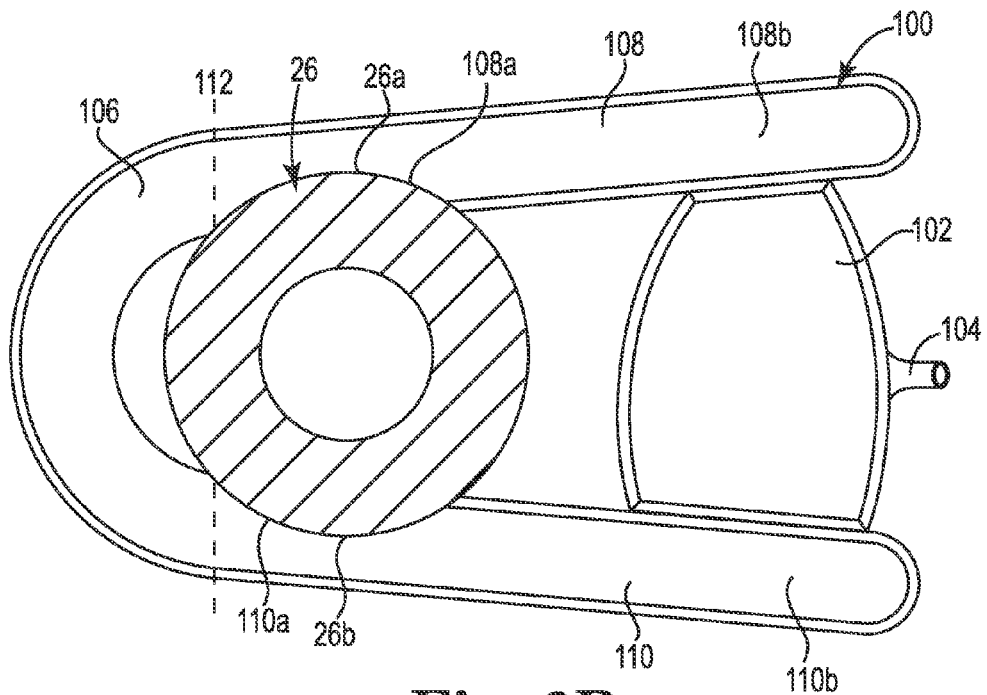
FIG. 2B is an end view of one embodiment of a clamp and an inflatable device situated on the urethra, where the inflatable device is expanded to open the urethra for voiding.
Figure 2C:
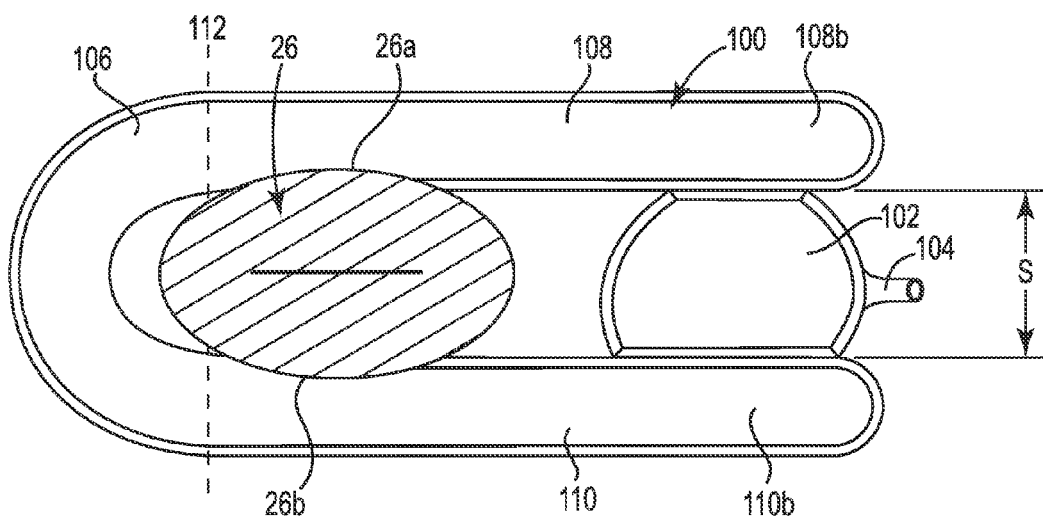
FIG. 2C is an end view of a clamp and an inflatable device situated on the urethra with the inflatable device deflated to coapt the urethra and maintain continence.

FIG. 2A is a perspective view and FIG. 2B is an end view of one embodiment of a clamp 100 and an inflatable device 102 situated on the urethra 26, where the inflatable device 102 is expanded to open the urethra 26 for voiding. FIG. 2C is an end view of the clamp 100 and the inflatable device 102 situated on the urethra 26 with the inflatable device 102 deflated to coapt the urethra 26 and maintain continence. The inflatable device 102 is provided with a connector 104 that is suitable for attachment to tubing, such as tubing 32 (shown in FIG. 1). In some embodiments, the clamp 100 is similar to the clamp 22 and/or the inflatable device 102 is similar to the inflatable device 24 (shown in FIG. 1).

The clamp 100 includes an end portion 106 connected to a first longitudinal portion 108 and a second longitudinal portion 110, which forms a C-shaped or close-pin shaped device that has a space or gap between the first longitudinal portion 108 and the second longitudinal portion 110. Each of the first and second longitudinal portions 108 and 110 is a rigid member that retains its shape. The end portion 106 is an elastic member that attempts to retain its initial shape such that the end portion 106 forces or biases the first longitudinal portion 108 and the second longitudinal portion 110 together or apart to maintain its shape and the initially formed space or gap between the first longitudinal portion 108 and the second longitudinal portion 110.

The clamp 100 is sized to fit around the urethra 26 and compress the urethra 26 when the inflatable device 102 is deflated. To put the clamp 100 around the urethra 26, the space S between the first longitudinal portion 108 and the second longitudinal portion 110 is expanded and the urethra 26 is slid between the first and second longitudinal portions 108 and 110. Upon expansion of the gap, the end portion 106 is elastically deformed and the clamp 100 is fit around the urethra 26, such that the first longitudinal portion 108 contacts one side 26a of the urethra 26 and the second longitudinal portion 110 contacts the other side 26b, opposing the one side 26a, of the urethra 26. In some embodiments, the first longitudinal portion 108 includes cupping 108a to receive the urethra 26 and, in some embodiments, the second longitudinal portion 110 includes cupping 110a to receive the urethra 26. In some embodiments, the end portion 106 is connected at 112 to the first longitudinal portion 108 and the second longitudinal portion 110, where the cupping 108a and 110a begin on the first longitudinal portion 108 and the second longitudinal portion 110, respectively.

As illustrated, the end portion 106 is radially curved to elastically bias the first longitudinal portion 108 and the second longitudinal portion 110 together to compress the urethra 26. In other embodiments, the end portion 106 can have a different shape, such as an oblong shape or a rectilinear shape that has two or more corners.

In some embodiments, the clamp 100 is formed as a unitary piece, from one piece of material, such as a plastic. In some embodiments, the clamp 100 can be made from multiple pieces of material, such that the end portion 106 is one piece, and each of the first and second longitudinal portions 108 and 110 is a separate piece. Also, in these embodiments, each of the pieces can be made out of the same or different materials.

The inflatable device 102 is secured between distal portions 108b and 110b of the first and second longitudinal portions 108 and 110, respectively. In other embodiments, the inflatable device 102 can be attached to each of the first and second longitudinal portions 108 and 110 at another location or in another way to provide expansion of the distance between the first and second longitudinal portions 108 and 110 as the inflatable device 102 is expanded.

In operation, as described in reference to FIG. 1, a pump such as pump 28 and a fluid reservoir such as fluid reservoir 30 move fluid from the fluid reservoir to the inflatable device 102. This expands the inflatable device 102 and separates the first and second longitudinal portions 108 and 110 to open the urethra 26 for voiding. The end portion 106 is elastically deformed as the inflatable device 102 is expanded to separate the first longitudinal portion 108 and the second longitudinal portion 110. After some time, the fluid is removed from the inflatable device 102 and the end portion 106 forces or biases the first and second longitudinal portions 108 and 110 together to compress the urethra 26 and prevent incontinence.

Figure 3A:
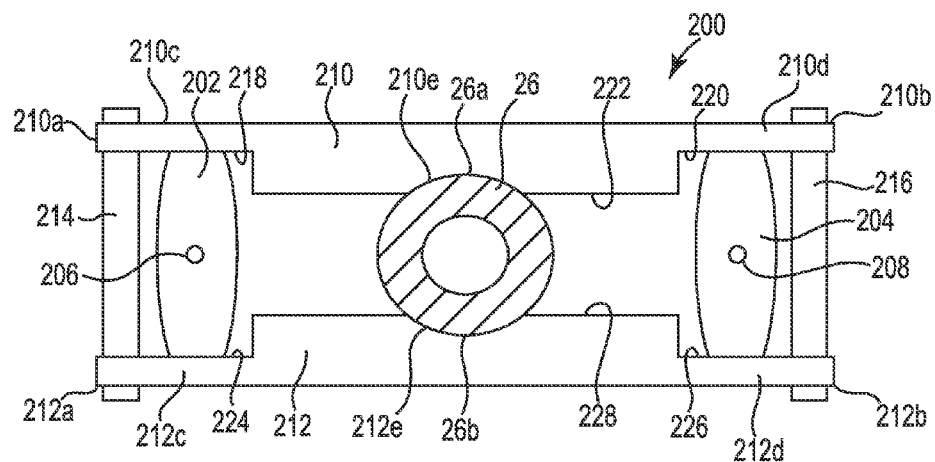
FIG. 3A is an end view of a clamp and inflatable devices situated on a urethra, where the inflatable devices are inflated to open the urethra for voiding.
Figure 3B:
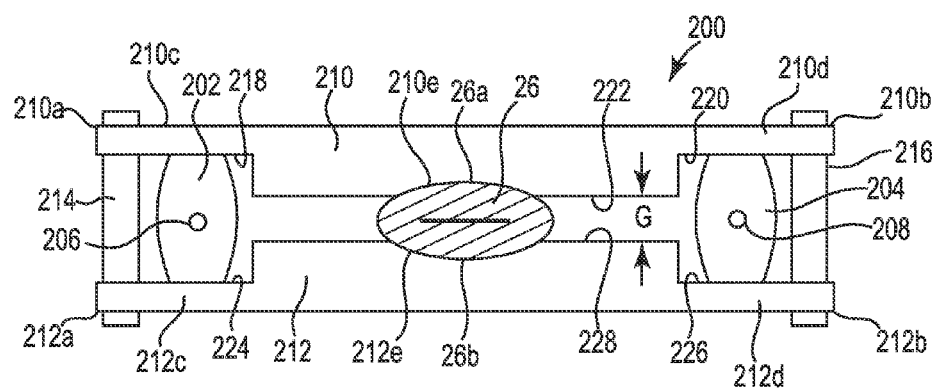
FIG. 3B is an end view of a clamp and inflatable devices situated on a urethra with the inflatable devices deflated to coapt the urethra and prevent incontinence.

FIGS. 3A and 3B are end views of one embodiment of a clamp 200 that includes multiple inflatable devices 202 and 204. FIG. 3A is an end view of the clamp 200 and the inflatable devices 202 and 204 situated on the urethra 26, where the inflatable devices 202 and 204 are inflated to open the urethra 26 for voiding. FIG. 3B is an end view of the clamp 200 and the inflatable devices 202 and 204 situated on the urethra 26 with the inflatable devices 202 and 204 deflated to coapt the urethra 26 and prevent incontinence. The inflatable devices 202 and 204 are provided with connectors 206 and 208, respectively, for attachment to tubing, such as tubing 32 (shown in FIG. 1). In some embodiments, the clamp 200 is similar to the clamp 22 and/or the inflatable devices 202 and 204 are similar to the inflatable device 24 (shown in FIG. 1).

The clamp 200 includes first and second rigid members 210 and 212 and first and second elastic devices 214 and 216. The first and second rigid members 210 and 212 include longitudinal member portions that engage the urethra 26 on opposing sides 26a and 26b of the urethra 26. Each of the first and second rigid members 210 and 212 is made from a rigid material that retains its shape.

The first and second elastic devices 214 and 216 are connected to the first and second rigid members 210 and 212. That is, the first elastic device 214 is connected at a first end 210a of the first rigid member 210 and at a first end 212a of the second rigid member 212, and the second elastic device 216 is connected at a second end 210b of the first rigid member 210 and at a second end 212b of the second rigid member 212. The first and second rigid members 210 and 212 fit around the urethra 26 and the first and second elastic devices 214 and 216 bias or force the first and second rigid members 210 and 212 together to compress the urethra 26 and prevent incontinence. Each of the first and second elastic devices 214 and 216 is a deformable elastic member, such as a spring or elastic material.

In some embodiments, the first and second elastic devices 214 and 216 are connected to the first and second rigid members 210 and 212 such that a space or gap G is formed between the first and second rigid members 210 and 212. In some embodiments, each of the first and second elastic devices 214 and 216 is a deformable elastic member that returns to its initial shape and that forces or biases the first and second rigid members 210 and 212 together or apart to maintain its shape and the initially formed space or gap G between the first and second rigid members 210 and 212.

As illustrated, each of the first and second rigid members 210 and 212 includes a step at each end portion of the rigid member and a raised plateau between the steps. The first rigid member 210 includes a first lower landing 218 at a first end portion 210c, a second lower landing 220 at a second end portion 210d, and a first upper or raised plateau 222 situated between the first and second lower landings 218 and 220. The first raised plateau 222 contacts the one side 26a of the urethra 26. The second rigid member 212 includes a first lower landing 224 at a first end portion 212c, a second lower landing 226 at a second end portion 212d, and a second upper or raised plateau 228 situated between the first and second lower landings 224 and 226. The second raised plateau 228 contacts another side 26b, opposing the one side 26a, of the urethra 26. In some embodiments, one or both of the first and second rigid members 210 and 212 is flat or otherwise curved to contact the urethra 26, such that the rigid member does not include a step or steps. In some embodiments, one or both of the first and second rigid members 210 and 212 includes a channel or cupping 210e and 212e, indicated in dashed lines, in the first and second raised plateaus 222 and 228, respectively, to receive the urethra 26.

As previously described, the clamp 200 is sized to fit around the urethra 26 and compress the urethra 26 when the inflatable devices 202 and 204 are deflated. To put the clamp 200 around the urethra 26, one of the rigid members, such as the second rigid member 212, is slid behind the urethra 26 and the other one of the rigid members, such as the first rigid member 210 is situated on the opposing side of the urethra 26. The first and second elastic devices 214 and 216 are connected to the ends of the first and second rigid members 210 and 212 and the first and second inflatable devices 202 and 204 are situated in place between the first and second rigid members 210 and 212. The clamp 200, including the first and second rigid members 210 and 212 and the first and second elastic devices 214 and 216, and the first and second inflatable devices 202 and 204 can be assembled in any suitable order. In some embodiments, one of the first and second elastic devices 214 and 216 is attached to the first and second rigid members 210 and 212 prior to situating one of the rigid members behind the urethra 26. In some embodiments one of the inflatable devices 202 and 204 is attached to the first and second rigid members 210 and 212 prior to situating one of the rigid members behind the urethra 26.

The first and second inflatable devices 202 and 204 are situated between the first and second rigid members 210 and 212. The first inflatable device 202 is situated between the first lower landings 218 and 224 and connected to each of the first lower landings 218 and 224. The second inflatable device 204 is situated between the second lower landings 220 and 226 and connected to each of the second lower landings 220 and 226. The first and second inflatable devices 202 and 204 are inflated with the fluid to expand the first and second elastic devices 214 and 216 and separate the first and second rigid members 210 and 212 to open the urethra 26 for voiding. The first and second inflatable devices 202 and 204 are deflated to allow the first and second elastic devices 214 and 216 to contract and force or bias the first and second rigid members 210 and 212 together to compress the urethra 26 and prevent incontinence.

In other embodiments, the inflatable devices 202 and 204 can be attached to each of the first and second rigid members 210 and 212 at another location or in another way, such as at each end or along the sides, to provide expansion of the distance between the first and second rigid members 210 and 212. In some embodiments, the inflatable devices 202 and 204 are inflated simultaneously. In some embodiments, the inflatable devices 202 and 204 are inflated synchronously, one at a time.

In operation, as described in reference to FIG. 1, a pump such as pump 28 and a fluid reservoir such as fluid reservoir 30 move fluid from the fluid reservoir to the inflatable devices 202 and 204. The inflatable devices 202 and 204 are inflated by the fluid, which expands the first and second elastic devices 214 and 216 and separates the first and second rigid members 210 and 212 to open the urethra 26 for voiding. After some time, the fluid is removed from the inflatable devices 202 and 204, which deflates the inflatable devices 202 and 204 and the first and second elastic devices 214 and 216 contract to force or bias the first and second rigid members 210 and 212 together to compress the urethra 26 and prevent incontinence.

Figure 4:
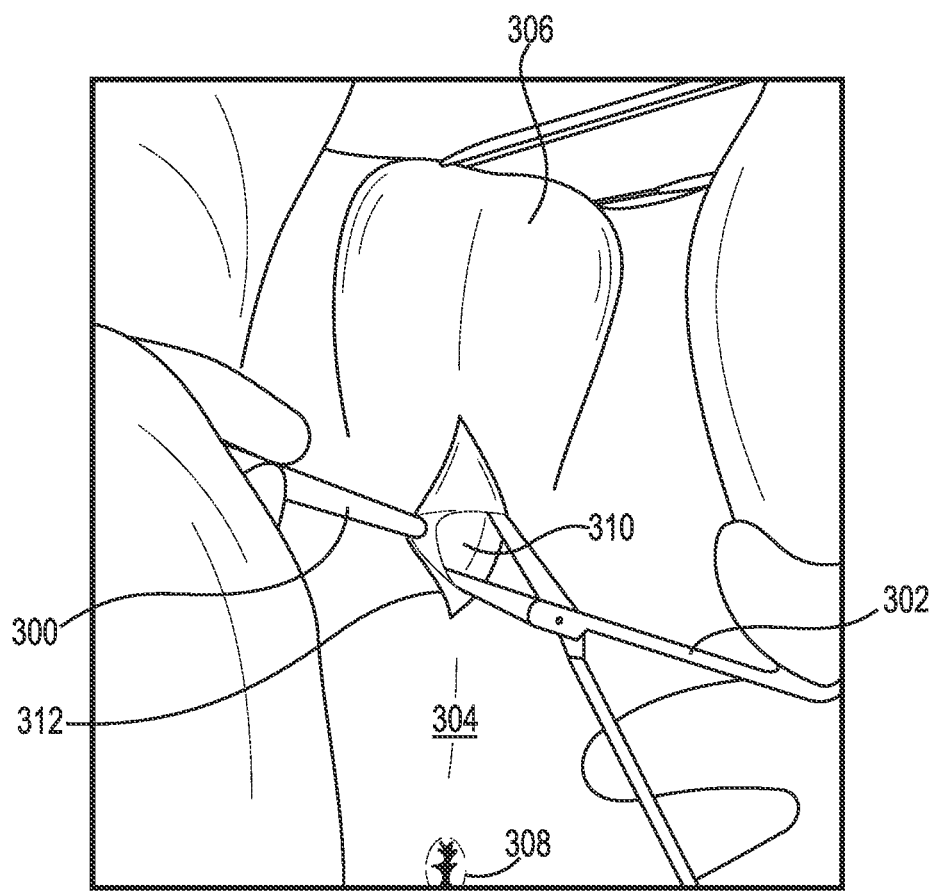
FIG. 4 is a schematic view of a scalpel and a dissection tool employed to dissect tissue through the perineum to expose the bulbar urethra.

FIG. 4 is a schematic view of a scalpel 300 and a dissection tool 302 employed to dissect tissue through the perineum 304, which is situated between the scrotum 306 and the anus 308, to expose the bulbar urethra 310. An incision 312 is made through the perineum 304 to dissect the tissue.

Figure 5:
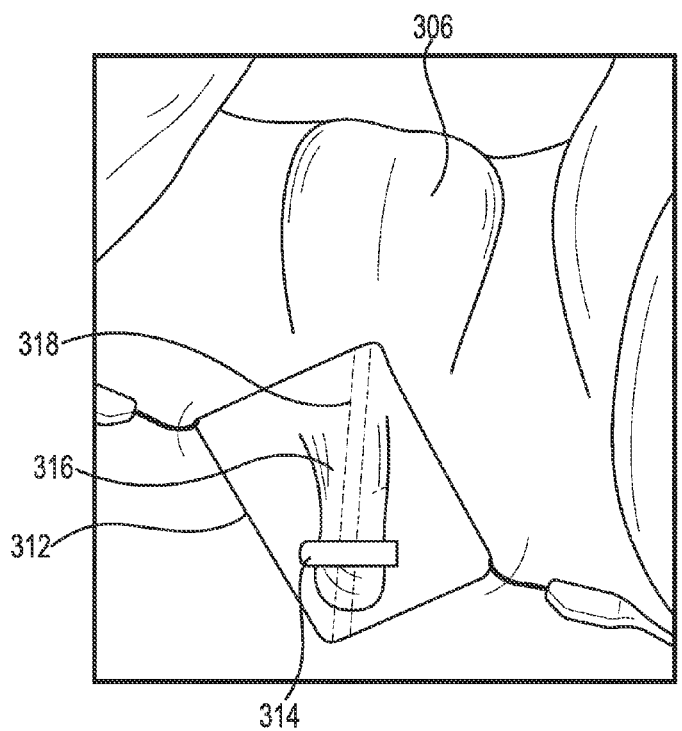
FIG. 5 is a schematic view of a clamp situated around the urethral bulb.

FIG. 5 is a schematic view of a clamp 314, such as one of the clamps 22, 100, and 200, situated around the urethral bulb 316. A urinary catheter 318 has been placed inside the bladder through the urethra to drain urine from the bladder, and the surgeon has dissected tissue away from and around the urethral bulb 316 for the suitable placement of the clamp 314.

Figure 6:
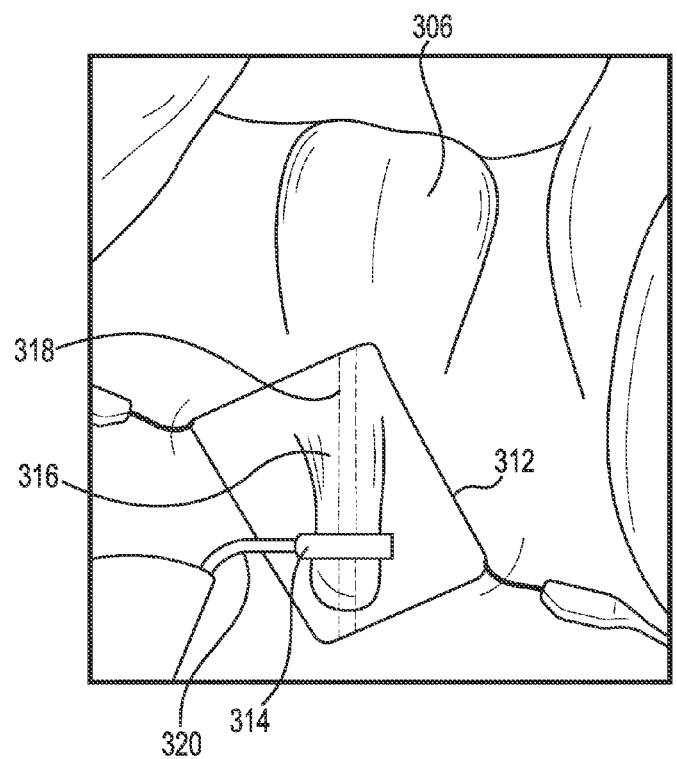
FIG. 6 is a schematic view of a clamp in place around the urethral bulb of the patient and connected to an AUS system.

FIG. 6 is a schematic view of the clamp 314 in place around the urethral bulb 316 of the patient and connected to an AUS system 320, similar to the AUS system 20 (shown in FIG. 1).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

The invention claimed is:

1. An artificial urinary sphincter system, comprising:
a clamp to be disposed on a urethra and including a first rigid member and a second rigid member;
a first elastic member biasing a first end of the first rigid member together with a first end of the second rigid member;
a second elastic member biasing a second end of the first rigid member together with a second end of the second rigid member, the first and second elastic members combining to elastically bias the first rigid member and the second rigid member together to compress the urethra;
a first device coupled to the first rigid member and the second rigid member, the first device being inflatable to push the first end of the first rigid member away from the first end of the second rigid member; and
a second device coupled to the first rigid member and the second rigid member, the second device being inflatable to push the second end of the first rigid member away from the second end of the second rigid member;
wherein the first rigid member and the second rigid member are separated by inflating the first device and the second device.

2. The system of claim 1, comprising:
a reservoir to hold a fluid; and
a pump to move the fluid from the reservoir to the first device to inflate the first device and push the first rigid member away from the second rigid member.

3. The system of claim 2, wherein the first device is to be drained of the fluid and the first rigid member and the second rigid member are elastically biased together by the first elastic member to compress the urethra as the fluid flows out of the first device.

4. The system of claim 1, wherein the first elastic device is coupled to the first rigid member and the second rigid member at one end of the clamp and the second elastic device is coupled to the first rigid member and the second rigid member at another end of the clamp to elastically bias together the first rigid member and the second rigid member.

5. The system of claim 1, wherein the first device and the second device are inflated simultaneously to separate the first rigid member and the second rigid member.

6. The system of claim 1, wherein the first elastic member is attached to the first rigid member adjacent to the first end of the first rigid member, and the first elastic member is attached to the second rigid member adjacent to the first end of the second rigid member, and wherein the second elastic member is attached to the first rigid member adjacent to the second end of the first rigid member, and the second elastic member is attached to the second rigid member adjacent to the second end of the second rigid member.

7. The system of claim 6, wherein the first device is attached to the first rigid member adjacent to the first end of the first rigid member, and the first device is attached to the second rigid member adjacent to the first end of the second rigid member, and wherein the second device is attached to the first rigid member adjacent to the second end of the first rigid member, and the second device is attached to the second rigid member adjacent to the second end of the second rigid member.

8. The system of claim 6, wherein the first device is attached to the first and second rigid members between the first elastic member and the second device, and wherein the second device is attached to the first and second rigid members between the first device and the second elastic member.

* * * * *